United States Patent
Kimoto

(10) Patent No.: US 11,596,061 B2
(45) Date of Patent: Feb. 28, 2023

(54) STRETCHABLE WIRING MEMBER

(71) Applicant: SEKISUI POLYMATECH CO., LTD., Saitama (JP)

(72) Inventor: Takaya Kimoto, Saitama (JP)

(73) Assignee: SEKISUI POLYMATECH CO., LTD., Saitama (JP)

( * ) Notice: Subject to any disclaimer, the term of this patent is extended or adjusted under 35 U.S.C. 154(b) by 0 days.

(21) Appl. No.: 15/734,021

(22) PCT Filed: Jun. 28, 2019

(86) PCT No.: PCT/JP2019/025973
§ 371 (c)(1),
(2) Date: Dec. 1, 2020

(87) PCT Pub. No.: WO2020/004660
PCT Pub. Date: Jan. 2, 2020

(65) Prior Publication Data
US 2021/0227689 A1      Jul. 22, 2021

(30) Foreign Application Priority Data

Jun. 28, 2018   (JP) .............................. JP2018-122745

(51) Int. Cl.
*H05K 1/02*  (2006.01)
*H05K 1/09*  (2006.01)
(Continued)

(52) U.S. Cl.
CPC .......... *H05K 1/0283* (2013.01); *A61B 5/268* (2021.01); *H05K 1/09* (2013.01); *H05K 1/11* (2013.01);
(Continued)

(58) Field of Classification Search
CPC .......... H05K 1/0283; H05K 1/09; H05K 1/11; H05K 2201/10151; H05K 1/02; A61B 5/268; A61B 5/681
See application file for complete search history.

(56) References Cited

U.S. PATENT DOCUMENTS

2008/0179079 A1    7/2008   Ishii et al.
2014/0299362 A1*  10/2014   Park ..................... H05K 1/0283
                                                                174/254
(Continued)

FOREIGN PATENT DOCUMENTS

JP   2008-112849 A   5/2008
JP   2012-033597 A   2/2012
(Continued)

OTHER PUBLICATIONS

Machine Translation: JP2014193267A, Published Oct. 9, 2014.*
International Search Report for PCT Patent App. No. PCT/JP2019/025973 (dated Aug. 20, 2019).

*Primary Examiner* — Ishwarbhai B Patel
(74) *Attorney, Agent, or Firm* — Cermak Nakajima & McGowan LLP; Tomoko Nakajima

(57) ABSTRACT

In a stretchable wiring member having a relatively hard portion, such as a contact point, there is provided a solution to malfunction of the stretchable wiring member caused by stress generated at a boundary between the hard portion and a flexible portion. A stretchable wiring member includes a flexible substrate having stretchability, a stretchable wiring line disposed along the flexible substrate and configured to be stretched in association with stretching deformation of the flexible substrate, and a hard member that is harder than the flexible substrate. The flexible substrate has an extension layer portion interposed between the hard member and the stretchable wiring line.

13 Claims, 10 Drawing Sheets

(51) Int. Cl.
  *H05K 1/11*   (2006.01)
  *A61B 5/268*   (2021.01)
  *H05K 1/03*   (2006.01)
  *H05K 1/18*   (2006.01)

(52) U.S. Cl.
  CPC ............ *H05K 1/0393* (2013.01); *H05K 1/18* (2013.01); *H05K 2201/0133* (2013.01); *H05K 2201/0323* (2013.01); *H05K 2201/10151* (2013.01)

(56) References Cited

U.S. PATENT DOCUMENTS

| | | | | |
|---|---|---|---|---|
| 2015/0348800 | A1* | 12/2015 | Cho | H01L 29/78603 257/66 |
| 2017/0245362 | A1* | 8/2017 | Iwase | H05K 3/4617 |
| 2018/0020936 | A1 | 1/2018 | Kwon et al. | |
| 2018/0027661 | A1* | 1/2018 | Ogura | H05K 1/038 361/749 |
| 2018/0077794 | A1* | 3/2018 | Iwase | H05K 3/361 |
| 2018/0092206 | A1* | 3/2018 | Iwase | H05K 1/0283 |
| 2018/0249576 | A1* | 8/2018 | Ogura | H05K 1/118 |
| 2019/0045627 | A1* | 2/2019 | Kikuchi | H01B 7/10 |

FOREIGN PATENT DOCUMENTS

| | | | |
|---|---|---|---|
| JP | 2014-193266 A | 10/2014 | |
| JP | 2014-193267 A | 10/2014 | |
| JP | 2016-145725 A | 8/2016 | |
| WO | WO2016/114298 A1 | 7/2016 | |

\* cited by examiner

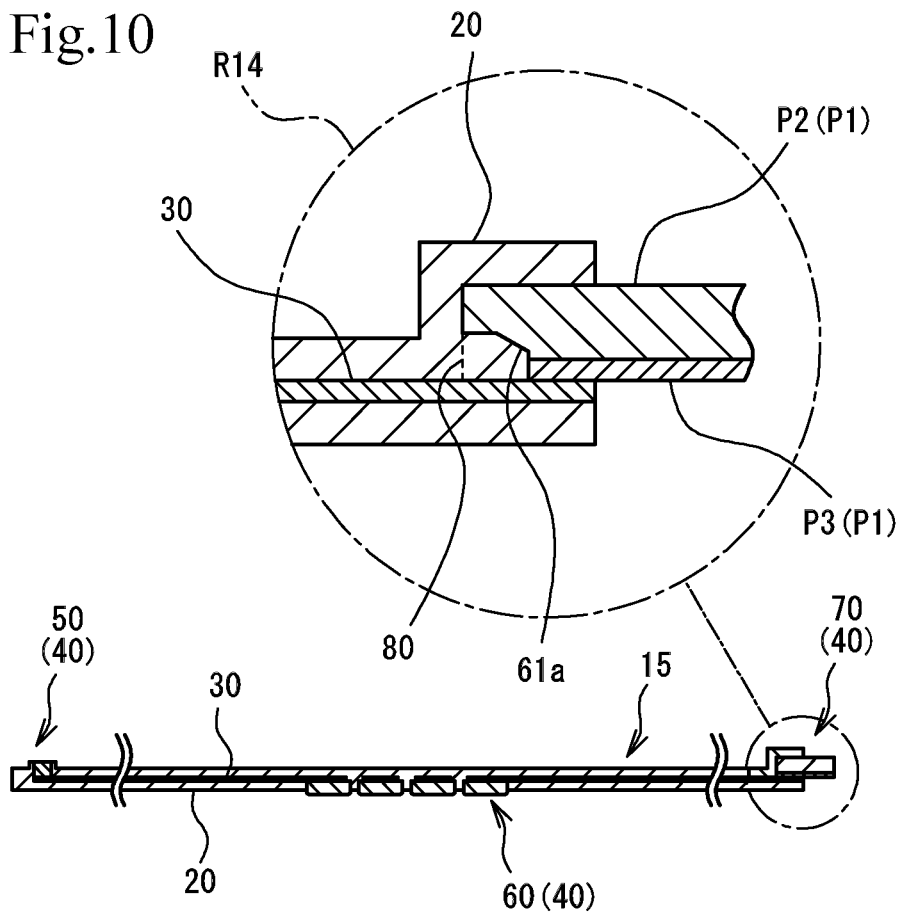
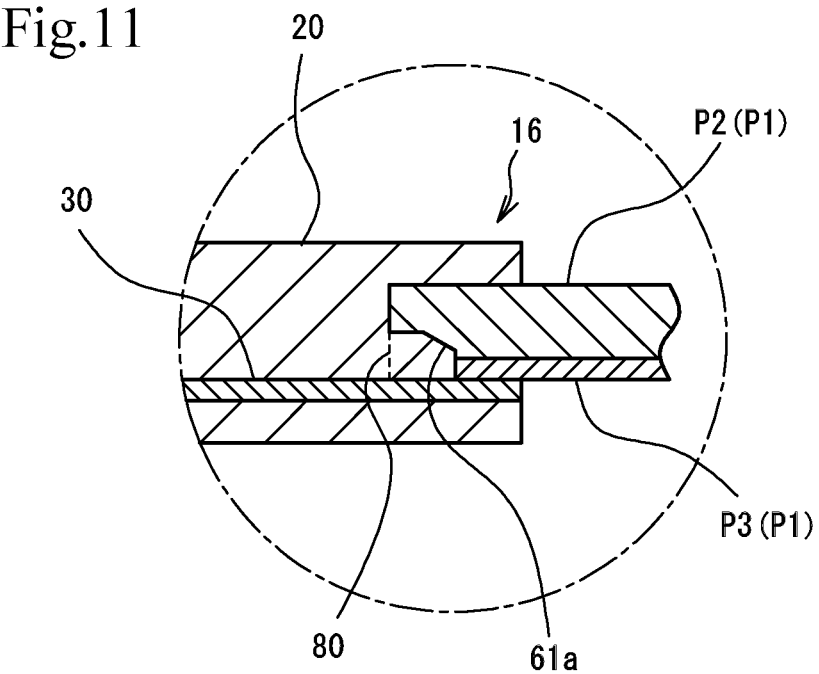

STRETCHABLE WIRING MEMBER

This application is a national phase entry under 35 U.S.C. § 371 of PCT Patent Application No. PCT/JP2019/025973, filed on Jun. 28, 2019, which claims priority under 35 U.S.C. § 119 to Japanese Patent Application No. 2018-122745, filed Jun. 28, 2018, both of which are incorporated by reference.

TECHNICAL FIELD

The present invention relates to a stretchable wiring member having a flexible substrate and stretchable wiring lines disposed at the flexible substrate.

BACKGROUND ART

Wearable devices, such as smart watches, activity meters, or pulsimeters, have been developed widely in recent years. Such wearable devices are equipped with sensors for measuring body conditions and activities, for example, by taking the pulse or by counting the number of walking steps. A typical wearable device includes a unit in which semiconductor devices are arranged in a flexible substrate or a rigid substrate. Such a wearable device does not follow body movement and may give an uncomfortable wearing feeling. On the other hand, a technique for obtaining a flexible wearable device has been developed. Such a flexible wearable device uses a stretchable wiring member in which stretchable electroconductive wires are formed on an elastic member or clothes having stretchability.

The stretchable wiring member used for the wearable device still has hard electrodes that serve as contact points. In this case, when the stretchable wiring member is stretched, stress is concentrated at the boundary between a contact point and the flexible substrate, which may cause the contact point to detach from the flexible substrate. If a stretchable electroconductive wire is laminated on a detached portion, the wire may break simultaneously with detachment. To solve this problem, disposing a reinforcement member is proposed by Japanese Unexamined Patent Application Publication No. 2012-033597 (PTL 1) and also by Japanese Unexamined Patent Application Publication No. 2016-145725 (PTL 2).

CITATION LIST

Patent Literature

PTL 1: Japanese Unexamined Patent Application Publication No. 2012-033597
PTL 2: Japanese Unexamined Patent Application Publication No. 2016-145725

SUMMARY OF INVENTION

Technical Problem

However, disposing the reinforcement member proposed by Japanese Unexamined Patent Application Publication No. 2012-033597 (PTL 1) or by Japanese Unexamined Patent Application Publication No. 2016-145725 (PTL 2) requires an area for fixation, which is not advantageous from the view point of size reduction. Accordingly, an object of the present invention is to provide another solution to the problem caused by stress generated at the boundary between a hard portion such as a contact point and a stretchable flexible portion that are included in a stretchable wiring member.

Solution to Problem

To solve the above problem, a stretchable wiring member according to an aspect of the present invention is configured as follows. The stretchable wiring member includes a flexible substrate having stretchability, a stretchable wiring line disposed along the flexible substrate and configured to be stretched in association with stretching deformation of the flexible substrate, and a hard member that is harder than the flexible substrate. In the stretchable wiring member, the flexible substrate has an extension layer portion interposed between the hard member and the stretchable wiring line.

The stretchable wiring member has the extension layer portion interposed between the hard member and the stretchable wiring line, which can prevent the stretchable wiring line from breaking easily.

In the case in which the flexible substrate has the hard member such as an electrode and the stretchable wiring line is connected to the electrode, there arises a problem that the stretchable wiring line breaks easily at the boundary with the electrode. However, providing the extension layer portion between the hard member and the stretchable wiring line causes the flexible substrate to start to stretch from the extension layer portion laminated on the hard member. As a result, the stretch of the flexible substrate does not start abruptly at the peripheral edge of the hard member but starts from a portion laminated on the hard member, which can reduce the stress concentrated on the stretchable wiring line at the boundary. Thus, the stretchable wiring member can prevent the stretchable wiring line from breaking easily. Accordingly, the stretchable wiring member, which does not use the reinforcement member of the known technique, can solve the problems of thickness and area increase and deterioration of the external appearance in association with provision of the reinforcement member.

The hard member may have a recess formed at a position between the hard member and the stretchable wiring line, and the extension layer portion may be disposed in the recess. Since the hard member has the recess, the extension layer portion can be formed as a lump that fills recess. The extension layer portion formed as the lump can be stretched more flexibly compared with an extension layer portion being simply formed as a thin layer between the hard member and the stretchable wiring line. When the hard member is about to be detached from the flexible substrate at the boundary therebetween in the stretchable wiring member, the extension layer portion serves as a buffer layer and can prevent the stretchable wiring line from breaking easily.

The hard member may be an electroconductive member. Since the hard member is the electroconductive member, the stretchable wiring member can be configured such that the stretchable wiring line is electrically connected to the hard member.

The hard member may be an electrode. Since the hard member is the electrode, the extension layer portion can be formed at the electrode of the stretchable wiring member. By disposing the extension layer portion between the flexible substrate and the electrode, the stretchable wiring member can reduce the stress generated at the boundary between the flexible substrate and the electrode and can prevent the stretchable wiring line from breaking easily even if the stretchable wiring member does not have the reinforcement member.

The hard member may be electrically connected to the stretchable wiring line. Since the hard member is electrically connected to the stretchable wiring line, the stretchable wiring member can be configured to have the extension layer portion at the boundary between the stretchable wiring line and the hard member. Accordingly, the stretchable wiring member can prevent the stretchable wiring line from breaking easily in the vicinity of the boundary at which the stretchable wiring line is connected to the hard member.

The hard member may be an electroconductive rubber that is made of at least one of a thermosetting rubber and a thermoplastic elastomer and in which an electroconductive filler is dispersed. In the stretchable wiring member, deformation of the electroconductive rubber can reduce part of the stress generated at the boundary between the hard member and the flexible substrate compared with a case in which the hard member is made, for example, of a hard resin or a metal. Accordingly, the stretchable wiring member can further prevent the stretchable wiring line from breaking easily in the vicinity of the boundary at which the stretchable wiring line is connected to the hard member.

The stretchable wiring line may extend from an outer periphery of the hard member in two opposite directions. With this configuration, the hard member can be disposed at an intermediate portion of the stretchable wiring line in the stretchable wiring member.

The stretchable wiring line may be spaced from the hard member in a thickness direction of the flexible substrate, and the stretchable wiring member may further include an isolation portion that isolates the stretchable wiring line from the hard member. The stretchable wiring line is spaced from the hard member, and the isolation portion that has no contact portion between the stretchable wiring line and the hard member is provided. Accordingly, even if the hard member is an electroconductive member, the stretchable wiring line can be laminated on the hard member while preventing an electrical connection between the stretchable wiring line and the hard member. Accordingly, multiple stretchable wiring lines can be disposed densely in a narrow area in the stretchable wiring member.

When stretchable wiring lines are patterned, using screen printing or the like, on a flexible substrate on which multiple contact point members are disposed, it is usually necessary to dispose a stretchable wiring line connected to a contact point member in such a manner that the stretchable wiring line detours around other contact point members. In this case, if a flexible substrate is, for example, shaped like a strip, it is necessary to dispose stretchable wiring lines near a side edge of the strip, which makes it difficult to dispose electrodes across the full width of the strip. In other words, disposing the stretchable wiring lines that detour around the electrodes requires an additional area, which inevitably increases the width of the strip. The stretchable wiring member, however, has the extension layer portions, and the extension layer portions enable stretchable wiring lines to be laminated on the electrodes without electrical connection therebetween.

The hard member may be an insulating member. Also in the case of the hard member serving as the insulating member, provision of the extension layer portion can prevent the stretchable wiring line from breaking easily. In other words, even in the case in which the stretchable wiring line is connected to the insulating member instead of the electroconductive member such as an electrode, the stretchable wiring line can be prevented from breaking easily. It may be necessary to connect the stretchable wiring line not only to the electroconductive member such as an electrode but also to an insulating member formed as, for example, a button having no electroconductivity. Even in this case, the stretchable wiring line can be prevented from breaking easily near the boundary between the insulating member and the stretchable wiring line.

The extension layer portion has an inner portion and an outer portion, in which the inner portion and the outer portion are defined with respect to the position in a projected area onto which the hard member is projected, and the outer portion may be formed to be thicker than the inner portion. In other words, the extension layer portion has a portion positioned near the center of the hard member and an outer portion when the hard member is viewed in plan, and the outer portion may be formed to be thicker than the portion near the center. With respect to the position in the projected area, the outer portion of the extension layer portion is formed to be thicker than the inner portion thereof. In other words, as viewed in plan, the extension layer portion has the portion positioned near the center of the hard member and the outer portion, and the outer portion is formed to be thicker than the portion near the center. With this configuration, the volume of the extension layer portion can be reduced compared with a case of an extension layer portion being formed so as to have a constant thickness. Also in this case, the stretchable wiring line can be effectively prevented from breaking easily. By changing the shape of the hard member, the outer portion of the extension layer portion can be made thicker easily than the inner portion with respect to the position in the projected area, in other words, thicker than the portion near the center of the hard member as viewed in plan, which leads to easy manufacturing.

The flexible substrate and the stretchable wiring line may contain a silicone rubber component. The flexible substrate and the stretchable wiring line contain the silicone rubber component, which improves adhesion between the flexible substrate and the stretchable wiring line and accordingly can prevent easy breakage of the stretchable wiring line.

Advantageous Effects of Invention

According to the present invention, the stretchable wiring line can be prevented from breaking easily.

BRIEF DESCRIPTION OF DRAWINGS

FIG. 4 are views illustrating portions of a stretchable wiring member according to a modification example 1-1, in which

FIG. 6 are cross-sectional views illustrating the stretchable wiring member of FIG. 5, in which

FIG. 8 are cross-sectional views illustrating the stretchable wiring member of FIG. 7, in which

FIG. 9 are cross-sectional views illustrating the stretchable wiring member of FIG. 7, in which

FIG. 10 is a cross-sectional view illustrating a stretchable wiring member according to a fourth embodiment, which corresponds to the cross-sectional view of FIG. 2.

FIG. 11 is a partially enlarged cross-sectional view illustrating a stretchable wiring member according to a modification example 4-1, which corresponds to a partially enlarged region R14 of FIG. 10.

FIG. 12 are views illustrating portions of a stretchable wiring member according to a fifth embodiment, in which

DESCRIPTION OF EMBODIMENTS

Example embodiments according to the present invention will be described with reference to the drawings. Note that the descriptions of the same material, composition, production method, advantageous effects, or the like will not be repeated for each embodiment described below. In addition, terms such as "first", "second", "third", or the like, will be used in the specification or in the appended claims with an intension to differentiate elements of the invention from each other and not with an intension to indicate a specific order nor to indicate that one is superior or inferior to another.

Figure 1:
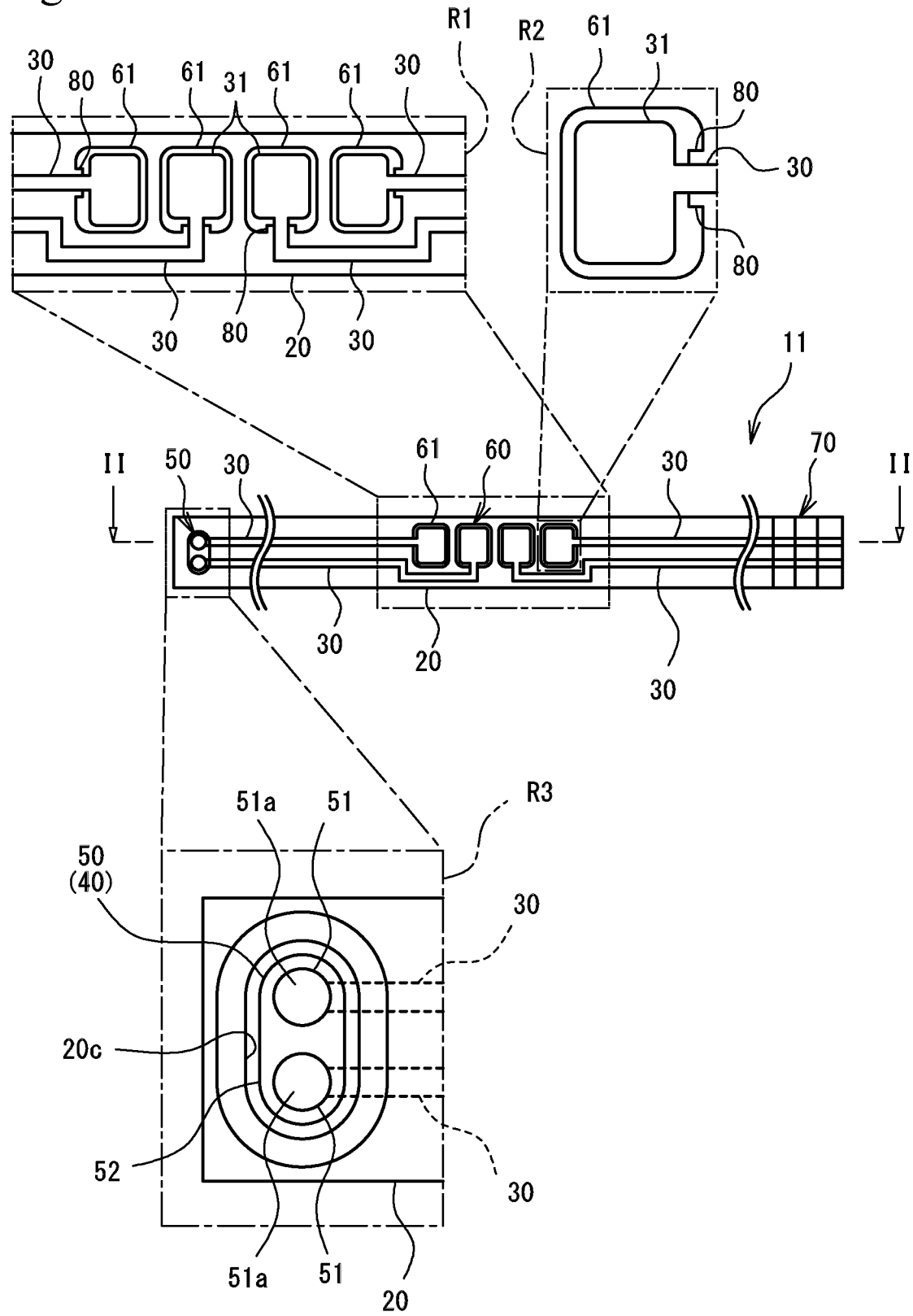
FIG. 1 is a schematic plan view illustrating a stretchable wiring member according to a first embodiment, in which a flexible substrate is assumed to be transparent.
Figure 2:
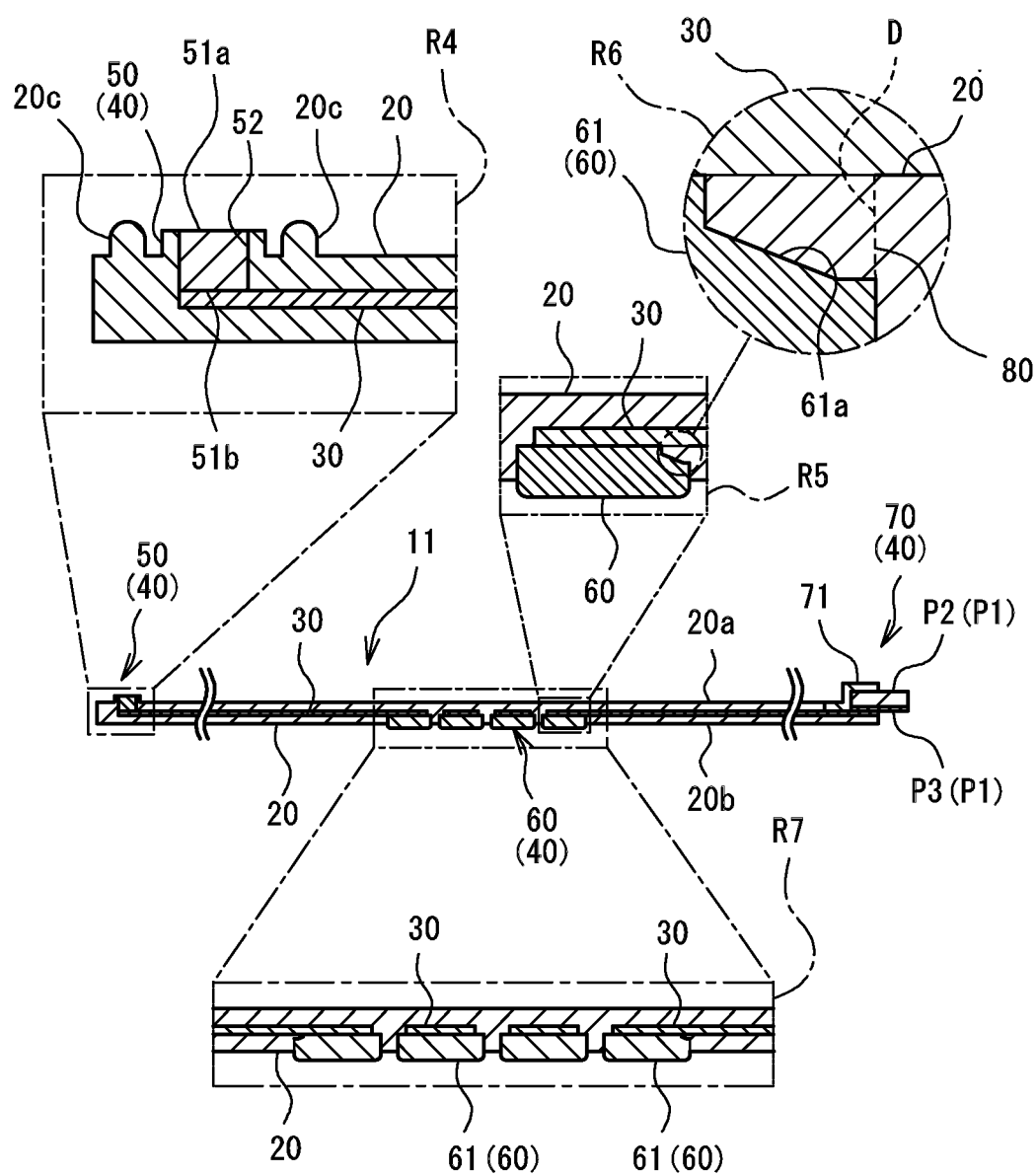
FIG. 2 is a cross-section of the stretchable wiring member taken along line II-II in FIG. 1.
Figure 3:
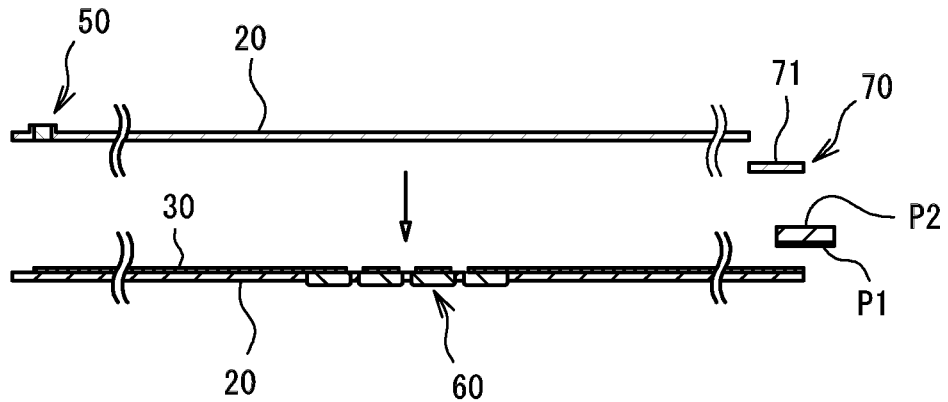
FIG. 3 is a diagram for explanation of a manufacturing method of the stretchable wiring member of FIG. 1.

First Embodiment [FIGS. 1 to 3]

A stretchable wiring member 11 according to the present embodiment will be described. FIG. 1 is a plan view of the stretchable wiring member 11 in which a flexible substrate 20 (to be described later) is assumed to be transparent. FIG. 2 is a cross-sectional view of the stretchable wiring member 11. The stretchable wiring member 11 includes a flexible substrate 20 that is stretchable and stretchable wiring lines 30 that are laminated on the flexible substrate 20. The stretchable wiring member 11 further includes contact point members 40 that include an electroconductive rubber connector 50, a body sensor 60, and a second connector 70. The electroconductive rubber connector 50 is electrically connected to the stretchable wiring lines 30. The contact point members 40 of the present embodiment are formed as hard members that are harder than the flexible substrate 20. Next, portions constituting the stretchable wiring member 11 will be described below.

Flexible Substrate 20: The flexible substrate 20 is a stretchable base member (stretchable substrate) that supports the stretchable wiring lines 30. The flexible substrate 20 is made of a flexible material, such as a thermosetting rubber or a thermoplastic elastomer, having insulating properties. The flexible substrate 20 is made of a stretchable material having such a stretchability that the flexible substrate 20 can return to its initial length after stretched at least to 120% or more, more preferably to 150% or more, of the initial length.

It is preferable that the hardness of the thermosetting rubber and thermoplastic elastomer be 90 or less in terms of A-hardness defined in JIS K6253 ("90" in this meaning is hereinafter termed as "A90"). If the rubber hardness exceeds A90, it may become difficult to achieve high stretchability because the stress generated by stretching becomes greater than necessary. The rubber hardness is preferably in the range of A0 to A70 from a view point of better stretchability, and more preferably in the range of A20 to A50 from a view point of better combination of stretchability and handling easiness.

The flexible substrate 20 may be shaped like a strip or a stick. The flexible substrate 20 may be made wide at a portion, and its vicinity, to which each contact point member 40 is fixed. The wide portion formed near each contact point member 40 can reduce the rate of extension of the flexible substrate 20 near the boundaries between the stretchable wiring lines 30 and each contact point member 40.

Stretchable Wiring Line 30: The stretchable wiring lines 30 are disposed in the flexible substrate 20 and can be stretched together with the flexible substrate 20. In the stretchable wiring member 11, the electroconductive rubber connector 50 and the second connector 70 are disposed at respective end portions of the flexible substrate 20 and electrically connected by the stretchable wiring lines 30 to the body sensors 60 disposed at the center of the flexible substrate 20. Accordingly, the electrical connection between the body sensors 60 and the electroconductive rubber connector 50 or the second connector 70 can be maintained in spite of changing the distance (length) between the body sensors 60 and the electroconductive rubber connector 50 or between the body sensors 60 and the second connector 70. Although the stretchable wiring lines 30 may be formed on the surface of the flexible substrate 20, the stretchable wiring lines 30 are preferably buried in the flexible substrate 20. The stretchable wiring lines 30 are thereby protected.

Each stretchable wiring line 30 is made of an electroconductive material having stretchability. More specifically, the stretchable wiring line 30 may be made of a flexible electroconductive resin in which an electroconductive filler, such as a silver filler, is dispersed in a thermosetting rubber or a thermoplastic elastomer. In the case of the flexible substrate 20 being made of a thermosetting rubber or a thermoplastic elastomer, the stretchable wiring line 30 is preferably made of a flexible electroconductive resin in which silver powder or carbon powder is dispersed in the same type of resin. This improves adherence between the flexible substrate 20 and the stretchable wiring line 30.

Both of the stretchable wiring line 30 and the flexible substrate 20 are made of flexible materials. The hardnesses of both materials can be set to be the same. The hardness of the stretchable wiring line 30, however, may be set higher than the hardness of the flexible substrate 20. In the stretchable wiring member 11 with this hardness configuration, when the stretchable wiring member 11 is compressed, the flexible substrate 20 is more vulnerable to compressive deformation than the stretchable wiring line 30. The stretchable wiring line 30 thereby do not change in volume easily. Accordingly, in an application in which the stretchable wiring member 11 is subjected to pressure in a direction different from the stretching direction, the stretchable wiring line 30 can exhibit stable electric resistance.

It is preferable that the adhesive strength between the stretchable wiring line 30 and the flexible substrate 20 be set to be greater than the tensile strength at break of the stretchable wiring line 30. If the tensile strength at break of the stretchable wiring line 30 is greater than the adhesive strength between the stretchable wiring line 30 and the flexible substrate 20, the stretchable wiring line 30 may be detached from the flexible substrate 20 when the stretchable wiring member 11 is elongated largely, for example, to a level exceeding 200%. In this case, the stretchable wiring line 30 deforms largely in the lateral direction thereof. Stresses are thereby generated between the stretchable wiring line 30 and the flexible substrate 20, which possibly causes the stretchable wiring line 30 to detach more readily.

To address this problem, the tensile strength at break of the stretchable wiring line 30 is set to be smaller than the adhesive strength between the stretchable wiring line 30 and the flexible substrate 20. As a result, cracks can occur in part of the stretchable wiring line 30 before the stretchable wiring line 30 is detached from the flexible substrate 20. These cracks, which are normally small, may cause the electric resistance to increase but do not easily lead to large cracks that break the stretchable wiring line 30. The breaking of the stretchable wiring line 30 can be thereby suppressed while suppressing the detachment of the stretchable wiring line 30. Moreover, the elongation limit of the stretchable wiring line 30 is detectable by monitoring the increase of electric resistance of the stretchable wiring line 30.

The above relationship between the adhesive strength and the tensile strength at break can be determined by performing tension tests on the stretchable wiring member 11 and observing crack generation in the stretchable wiring line 30 before the stretchable wiring line 30 is detached. In other words, if the stretchable wiring line 30 is detached before cracks are generated in the stretchable wiring line 30, the tensile strength at break of the stretchable wiring line 30 can be regarded as being greater than the adhesive strength between the stretchable wiring line 30 and the flexible substrate 20. On the other hand, if cracks are generated in part of the stretchable wiring line 30 before the stretchable wiring line 30 is detached, the adhesive strength between the stretchable wiring line 30 and the flexible substrate 20 can be regarded as being greater than the tensile strength at break of the stretchable wiring line 30.

Contact Point Member 40: The contact point members 40 are connector portions of the stretchable wiring member that electrically connect the stretchable wiring lines 30 to connection objects P, such as a human body or an electronic device or component like a circuit board. The material used for the electroconductive portion of each contact point member 40 may be, for example, a metal, a carbon material, an electroconductive resin, an electroconductive rubber, or other electroconductive materials. Among these, the electroconductive resin is a resin in which an electroconductive filler is dispersed. The electroconductive rubber is a thermosetting rubber or a thermoplastic elastomer in which an electroconductive filler is dispersed. The electroconductive material is insulating resin particles or the like coated with a metal. It is preferable that the metal and the electroconductive filler described above be stable materials having such a high corrosion resistance that the metal and the electroconductive filler exhibit sufficient weatherability and durability even when the contact point member 40 is exposed out of the stretchable wiring member 11. For example, a noble metal such as gold or an alloy such as stainless steel, or carbon powder can be used for this purpose.

The stretchable wiring member 11 of the present embodiment uses three types of the contact point members 40, in other words, the electroconductive rubber connector 50, the body sensors 60, and the second connector 70. Each contact point member 40 has a hard portion that is harder than the flexible substrate 20.

Electroconductive Rubber Connector 50: Among the connector portions of the stretchable wiring member 11 for electrical connection with the connection objects P, such as a circuit board, the electroconductive rubber connector 50 is a portion that includes an electrode 51 formed of an electroconductive rubber composite in which an electroconductive filler is dispersed in a rubber-like polymer.

The electroconductive rubber connector 50 has a first contact end 51a to be electrically connected to a connection object P and a second contact end 51b to be electrically connected to the stretchable wiring line 30. The electroconductive rubber connector 50 has the electrode 51 formed between the first contact end 51a and the second contact end 51b, and the electrode 51 electrically connects the connection object P to the stretchable wiring line 30. The electroconductive rubber connector 50 is deformable in the direction of the electrode 51 extending from the first contact end 51a to the second contact end 51b. The electroconductive rubber connector 50 is sandwiched and pressed between a component such as a housing W and the connection object P such as a circuit board to which the stretchable wiring member 11 is electrically connected. The stretchable wiring member 11 of the present embodiment has a waterproofing rib 20c that is formed of the flexible substrate 20 so as to surround the electroconductive rubber connector 50 and protrude from a front surface 20a of the flexible substrate 20. The other surface of the flexible substrate 20 opposite to the front surface 20a is a back surface 20b.

The electroconductive rubber composite that constitutes the electroconductive rubber connector 50 can be obtained by dispersing an electroconductive filler in a liquid polymer composite, placing the composite in a magnetic field and orienting (or aligning) electroconductive filler particles in an electric connection direction, and solidifying the liquid polymer composite. Thus, the electroconductive rubber composite has the electrode 51 that is surrounded by an insulating cover portion 52 formed of the solidified polymer composite. In the electrode 51, the electroconductive filler particles are continuously connected. When the electrode 51 is observed as a whole, it seems that the electrode 51 is made only of the electroconductive filler. When the electrode 51 is observed closely, however, the electroconductive filler particles are oriented inside the rubber-like elastic body. Accordingly, even if the amount of the electroconductive filler mixed therein is small, the electric resistance of the electrode 51 can be reduced while the electrode 51 has an appropriate flexibility. The electroconductive rubber composite, in which the electroconductive filler particles are dispersed in a rubber-like polymer material, also can be obtained in a way different from the above, in other words, by dispersing electroconductive filler particles uniformly in a flexible polymer material.

The rubber-like elastic body fills spaces among the electroconductive filler particles of the electrode 51 is made of the same material as that of the cover portion 52. An example of the electroconductive filler is granular, fibrous, fragmental, or filamentous metal particles. More specifically, the electroconductive filler may be particles of nickel, cobalt, iron, ferrite, or an alloy containing a large amount of these metals, or particles of a highly conductive metal such as gold, silver, platinum, aluminum, copper, iron, palladium, chromium, or of an alloy such as stainless steel, or particles of a resin or ceramic powder or fiber coated with a magnetic electroconductive material, or a magnetic electroconductive particles of which the particles are coated with a highly conductive metal. The metal particles may have an average diameter of approximately 1 to 200 μm. In this range, particles can be efficiently oriented, and can enter a linked state, in directions parallel to lines of magnetic force in the magnetic field generated in a molding die.

The cover portion 52 is integrated with the electrode 51 so as to cover and protect the electrode 51 except for exposed portions that serve as contact points. The cover portion 52 is formed of an insulating rubber-like elastic body. For example, the material of the rubber-like elastic body may be natural rubber or silicone rubber, isoprene rubber, butadiene rubber, acrylonitrile-butadiene rubber, 1,2-polybutadiene, styrene-butadiene rubber, chloroprene rubber, nitrile rubber, butyl rubber, ethylene-propylene rubber, chlorosulfonated rubber, polyethylene rubber, acrylic rubber, epichlorohydrin rubber, fluoro rubber, urethane rubber, styrenic thermoplastic elastomer, olefinic thermoplastic elastomer, polyester thermoplastic elastomer, polyurethane thermoplastic elastomer, polyamide thermoplastic elastomer, polyvinyl chloride thermoplastic elastomer, thermoplastic fluoroelastomer, or ionically crosslinked thermoplastic elastomer. Of these materials, a silicone rubber is preferable because the silicone rubber has good electrical insulation and favorable environmental characteristics. In addition, in the case of the electroconductive rubber connector 50 being produced by heating the material in a die, it is preferable to use a thermosetting rubber. It is more preferable to use a silicone rubber or a fluoro rubber because of their thermal resistance.

The hardness of the cover portion 52 is preferably in the range of 5 to 70 in A-hardness in accordance with JIS K6253, and more preferably in the range of 15 to 50. If the hardness exceeds 25 in A-hardness, compression of the electroconductive rubber connector 50 requires an increased amount of compressive load, which thereby increases the load applied to the connection object P and to the housing W. If the hardness is lower than 5.0 in A-hardness, the electroconductive rubber connector 50 is smashed and buckled easily when compressed, which tends to separate the particles easily from each other and may not provide stable conductivity.

The waterproofing rib 20c is a portion to be positioned between the flexible substrate 20 and the connection object P. When the waterproofing rib 20c is brought into press contact with the connection object P by pressing the stretchable wiring member 11, the waterproofing rib 20c isolates the electrode 51 from outside and prevents water from entering the electrode 51. The waterproofing rib 20c of the present embodiment protrudes from the front surface 20a of the flexible substrate 20. The waterproofing rib 20 is a continuous protrusion shaped like a ring as viewed in plan. Due to the waterproofing rib 20c being provided around the electroconductive rubber connector 50, the stretchable wiring member 11 can reduce the negative impact of water even in a splashing water environment, which can expand the application area of the stretchable wiring member 11.

Second Connector 70: The stretchable wiring member 11 has a connector portion to be electrically connected to a connection object P, such as a circuit board. The second connector 70 is a portion that is directly fixed, using a holding member 71, to a terminal portion P2 of a flexible cable P1 or the like.

The stretchable wiring lines 30 of the stretchable wiring member 11 are electrically connected to wiring P3 of the terminal portion P2 included in the connection object P. The holding member 71 fixes the stretchable wiring member 11 to the connection object P to maintain an electrical connection. The terminal portion P2 is formed of a resin film or the like, and the wiring P3 is formed of a metallic foil, such as copper foil. The holding member 71, which is made of a rubber material having flexibility, such as silicone rubber, is fixed to the flexible substrate 20 of the stretchable wiring member 11 and also to the terminal portion P2 of the connection object P.

Body Sensor 60: Among the connector portions of the stretchable wiring member 11 for electrical connection with the connection objects P, such as a circuit board, the body sensor 60 is a portion to be brought into contact, for example, with human skin surface. The electrode 61 of the body sensor 60 has an outer shape slightly larger than the electroconductive rubber connector 50 and is designed to have a large contact area to be in contact with an object such as skin. The body sensor 60 can be provided when the stretchable wiring member 11 is applied, for example, to measure body surface potentials. The electrode 61 of the present embodiment serves as a "hard member" according to the present invention. The large contact area can reduce stress concentration on the skin surface to be in contact with and improve contact stability when the electrode 61 is brought into close contact with the skin of human body to measure surface potentials. If the electrode 61 were formed like a metallic pin having a narrow contact point, stress would be concentrated at the point, giving an uncomfortable fit feeling. The electrode 61 is required to have a more or less large area.

The electrode 61 has a recess 61a formed therein. The recess 61a is formed by chipping off an edge portion of the electrode 61 located near the stretchable wiring line 30. Accordingly, if the electrode 61 is projected on a picture plane in the thickness direction of the flexible substrate 20, the recess 61a is present within the boundary of the projected electrode 61. An extension layer portion 80 of the flexible substrate 20, which will be described later, is formed as a filling portion for filling the recess 61a. A contact portion 31 is formed on the body sensor 60. The contact portion 31 is made of the same material as that of the stretchable wiring line 30 and has such a shape that an end portion of the stretchable wiring line 30 is expanded in the width direction thereof, which enables electrical contact in a wide area between the stretchable wiring line 30 and the body sensor 60.

The electrode 61 of the body sensor 60 is different from the electrode 51 of the electroconductive rubber connector 50 in the following points. The electrode 61 of the body sensor 60 is a contact point member 40 of which the electroconductive filler is carbon powder. Accordingly, the electrode 61 is superior in corrosion resistance and weatherability. The electrode 61 is slightly harder than the electrode 51 of the electroconductive rubber connector 50 and exhibits a resistance higher than that of the stretchable wiring line 30. The electrode 61, of which the conductive portion is made of the carbon material, has a higher electrical resistance than that of the stretchable wiring line 30. The electrode 61 is preferably formed so as to have a constant distance between the stretchable wiring line 30 and the contact surface of the electrode 61 to be in contact with the skin, and the stretchable wiring line 30 is preferably laminated on the body sensor 60 in an area as wide as possible. This enables the resistance to be constant between the stretchable wiring line 30 and the contact surface of the electrode 61 to be in contact with the skin, whatever portion of the electrode 61 the skin comes into contact with. That is why the stretchable wiring line 30 has the wide contact portion 31.

Extension Layer Portion 80: The extension layer portion 80 is a portion provided for the purpose that the flexible substrate 20 cannot come off easily from the connection surface with a hard portion, such as the electrode 61 of the contact point member 40. As illustrated in the partially enlarged regions R5 and R6 of FIG. 2, the extension layer portion 80 is formed as a thick filling portion that fills the recess 61a of the electrode 61. The extension layer portion 80 is formed so as to come into contact with the inside surface of the recess 61a and also with the surface of the stretchable wiring line 30 that faces the recess 61a. Accordingly, if the electrode 61 is projected on a picture plane in the thickness direction of the flexible substrate 20, the extension layer portion 80 is positioned within the projected area of the electrode 61, in other words, positioned inside the outer periphery (circumference) of the electrode 61 when viewed in plan. Put it another way, the extension layer portion 80 is formed as a laminated portion laminated on the upper surface of the electrode 61 (i.e., the inside surface of the recess 61a). The upper surface of the extension layer portion 80 forms the contact surface with the stretchable wiring line 30. The stretchable wiring member 11 has a protruding portion (i.e., extension layer portion 80) of which part of the flexible substrate 20 protrudes along the stretchable wiring line 30 into the recess 61a of the electrode 61. In other words, the extension layer portion 80 is formed as the protruding portion that protrudes into the electrode 61 from a boundary surface D that is the circumferential surface of the electrode 61 (i.e., the outer periphery of the above-described projected area).

Although the extension layer portion 80 is described as a portion of the flexible substrate 20, the extension layer portion 80 may be made of a material different from that of the flexible substrate 20 insofar as the material is more flexible than the electrode 61. In addition, although the extension layer portion 80 is described as being disposed between the flexible substrate 20 and the electrode 61, the extension layer portion 80 may be disposed between the stretchable wiring line 30 and a hard member other than the electrode 61. For example, the electroconductive rubber connector 50 and the second connector 70 may be formed as hard members. In this case, a recess may be formed at each hard member, and the extension layer portion 80 may be formed so as to fill the recess.

As the electrode 61 is viewed in plan, the boundary of a contact area between the stretchable wiring line 30 and the electrode 61 is positioned inside the outer periphery of the electrode 61. In other words, the contact portion 31 of the stretchable wiring line 30 is positioned so as to fit within the upper surface area of the electrode 61 (in other words, positioned inside the circumference of the upper surface of the electrode 61). Accordingly, when the stretchable wiring member 11 is stretched, the extension layer portion 80 can mitigate the stress generated on the boundary surface between the flexible substrate 20 and the electrode 61 and thereby prevent the stretchable wiring line 30 from breaking.

The body sensor 60 (the electrode 61) has a recess 61a formed where the extension layer portion 80 is disposed. Put it another way, the extension layer portion 80 is a portion of the flexible substrate 20 that enters the recess 61a formed in the body sensor 60. As described above, the recess 61a is formed in the body sensor 60, and the flexible substrate 20 is formed so as to enter the recess 61a. In addition, the surface of the flexible substrate 20 and the surface of the body sensor 60 are made so as to be flush with each other. This enables the stretchable wiring lines 30 to be formed, for example, by printing. This makes the manufacturing easier.

Next, a manufacturing method of the stretchable wiring member 11 will be described. The stretchable wiring member 11 can be manufactured in various ways. One example is described as follows. As illustrated in FIG. 3, a first segment of the flexible substrate 20 is produced. To produce the first segment, the flexible substrate 20 having a half thickness is molded integrally with the electrodes 61 of the body sensors 60. Subsequently, the stretchable wiring lines 30 and the contact portions 31 are printed on the surface of the first segment, for example, by screen printing. A second segment of the flexible substrate 20 is also produced. To produce the second segment, the flexible substrate 20 having a half thickness is formed integrally with the electroconductive rubber connector 50, for example, by insert molding. Subsequently, the second segment is adhered onto the first segment. The second connector 70 is formed when the first segment and the second segment are adhered to each other. The terminal portion P2 of the flexible cable P1 is inserted between the first segment and the second segment, and the terminal portion P2 is fixed using a holding member 71. The stretchable wiring member 11 can be thus manufactured. According to this manufacturing method, the flexible substrate 20 is molded integrally with the electrodes 61 and the electroconductive rubber connector 50. As a result, the electrodes 61 and the electroconductive rubber connector 50 can be integrated firmly into the flexible substrate 20, which can reduce the likelihood of the electrodes 61 and the electroconductive rubber connector 50 being detached from the flexible substrate 20 by repeated stretching deformation of the flexible substrate 20.

The electroconductive rubber connector 50 in which the electrode 51 and the cover portion 52 are integrally formed can be manufactured in advance, for example, by injecting a polymer liquid with an electroconductive filler mixed therein into a molding die, forming conduction paths by orienting the electroconductive filler by magnetic poles disposed in the molding die, and then solidifying the polymer liquid. The electroconductive rubber connector 50 is subsequently integrated into the second segment of the flexible substrate 20 as described above. Alternatively, the electroconductive rubber connector 50 may be formed simultaneously when the second segment of the flexible substrate 20 is formed. Still alternatively, an electroconductive rubber having a predetermined electric resistance may be formed in advance into the shape of the electrode 51.

The stretchable wiring member 11 obtained as described above has the extension layer portion 80 formed at the boundary between each electrode 61 and the stretchable wiring line 30 extending from the electrode 61. As a result, the extension layer portion 80 mitigates the stress concentrated at the boundary when the stretchable wiring member 11 is stretched, which can prevent the stretchable wiring line 30 from breaking easily in the vicinity of the boundary.

Figure 4A:
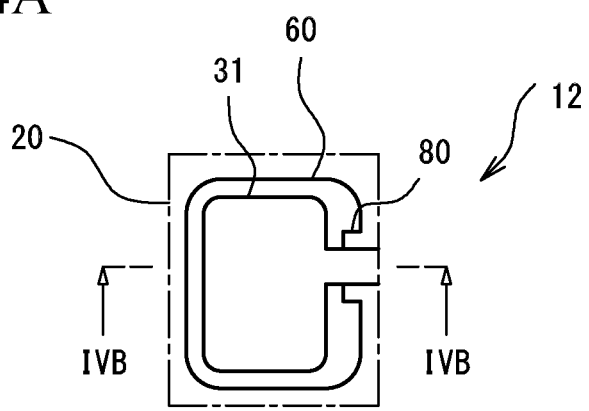
FIG. 4A is a partially enlarged plan view corresponding to a partially enlarged region R2 of FIG. 1
Figure 4B:
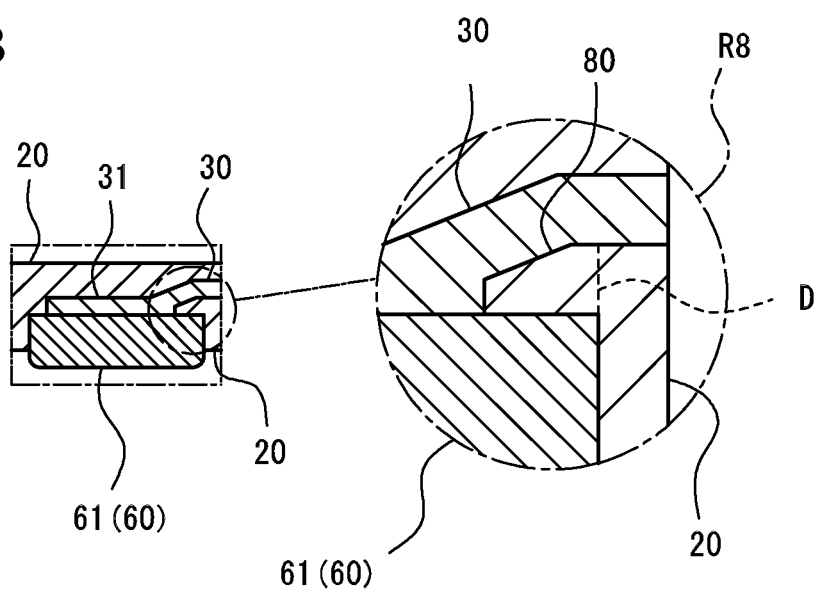
FIG. 4B is a partially enlarged cross-sectional view corresponding to a partially enlarged region R5 of FIG. 2.

Modification Example 1-1 [FIGS. 4]

A stretchable wiring member 12 of the present embodiment is different from the stretchable wiring member 11 of the first embodiment in that the extension layer portion 80 and its vicinity are configured differently. In other words, as illustrated in the enlarged views of the body sensor 60 of FIG. 4, the extension layer portion 80 is laminated on the flat upper surface of the electrode 61 of the body sensor 60. The stretchable wiring line 30 is formed so as to extend obliquely upward and climb the extension layer portion 80 from the contact portion 31 that is in electrical contact with the electrode 61. Also with this configuration of the stretchable wiring member 12, the extension layer portion 80 can mitigate the stress concentrated at the boundary between the electrode 61 and the stretchable wiring line 30, which can prevent the stretchable wiring line 30 from breaking easily in the vicinity of the boundary.

Figure 5:
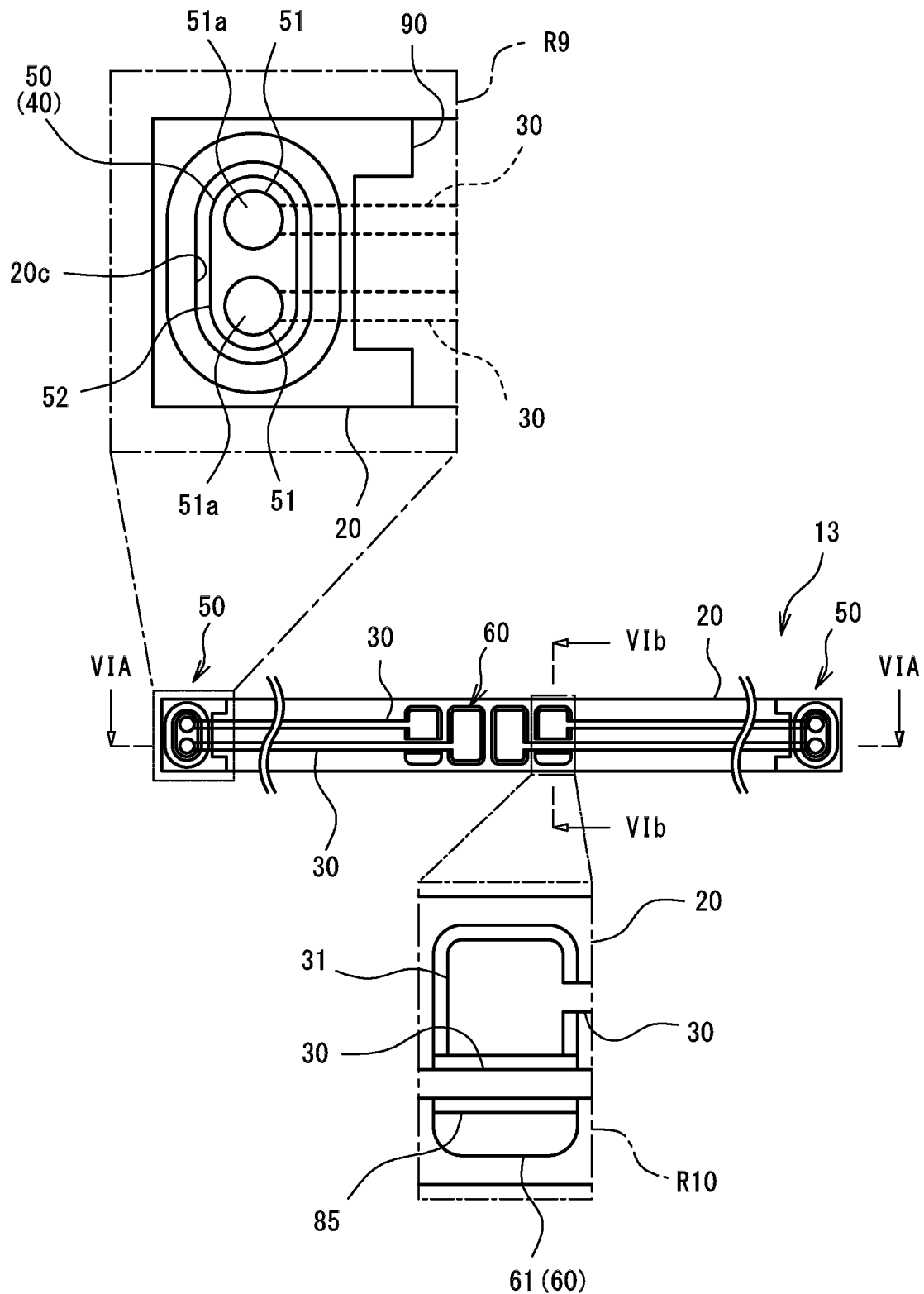
FIG. 5 is a schematic plan view illustrating a stretchable wiring member according to a second embodiment, in which a flexible substrate is assumed to be transparent.
Figure 6A:
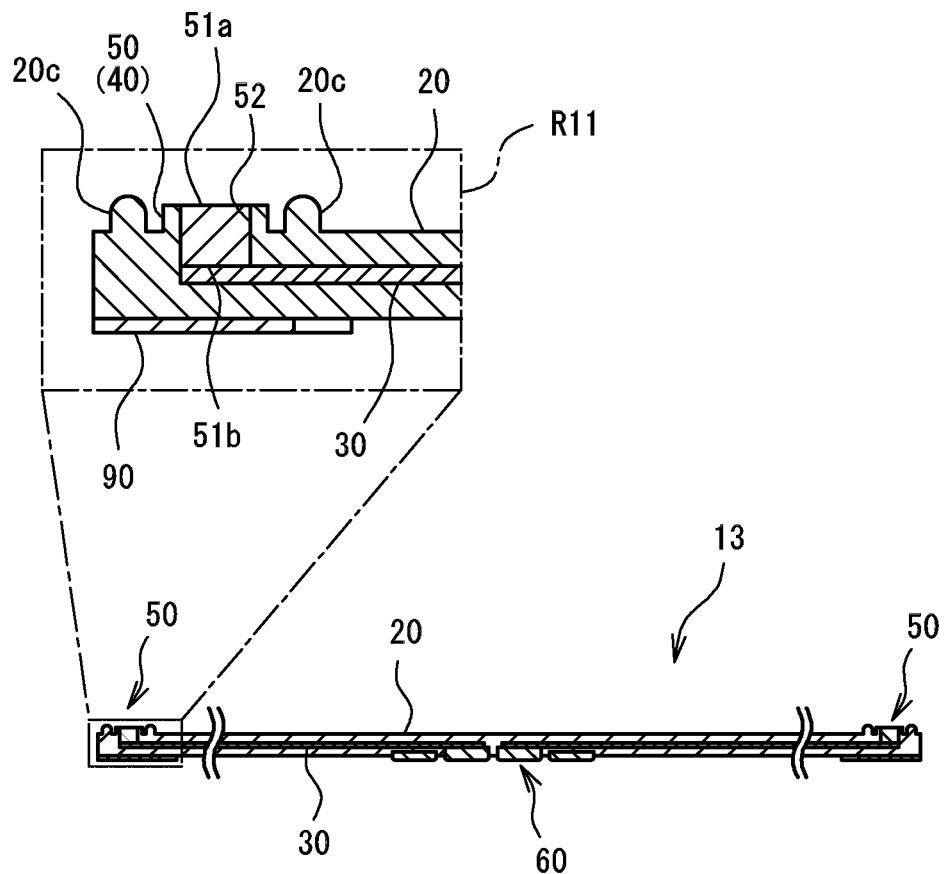
FIG. 6A is a cross section taken along line VIA-VIA in FIG. 5

Second Embodiment [FIGS. 5 to 6]

FIG. 5 is a plan view of a stretchable wiring member 13 in which the flexible substrate 20 is assumed to be transparent. FIG. 6 are cross-sectional views of the stretchable wiring member 13. Compared with the stretchable wiring member 11 of the first embodiment, the stretchable wiring member 13 of the present embodiment has a different configuration near the body sensor 60. In other words, the stretchable wiring line 30 extending from a second body sensor 60 is disposed so as to overlap a first body sensor 60. In the present embodiment, an extension layer portion 85 is provided at a position at which the stretchable wiring line 30 extending from the second body sensor 60 overlaps the first body sensor 60. The extension layer portion 85 enables the stretchable wiring line 30 connected to the second body sensor 60 to be disposed over the electrode 61 of the first body sensor 60 in an electrically isolated manner.

Regarding the stretchable wiring member 11, the contact point members 40, such as body sensors 60, were required to be disposed in a limited area in response to the demand of size reduction. In addition, it was difficult to adopt a multilayer arrangement of the stretchable wiring lines 30 due to cost limitation and avoidance of a warping problem. Under this situation, it was necessary to lay out the stretchable wiring lines 30 flatly in such a manner that a stretchable wiring line 30 connected to a far side electrode 61 was disposed so as to detour around a near side electrode 61, as is the case for the stretchable wiring member 11 described in the first embodiment. The configuration of the present embodiment, however, can eliminate the necessity of the stretchable wiring lines 30 detouring around.

Figure 6B:
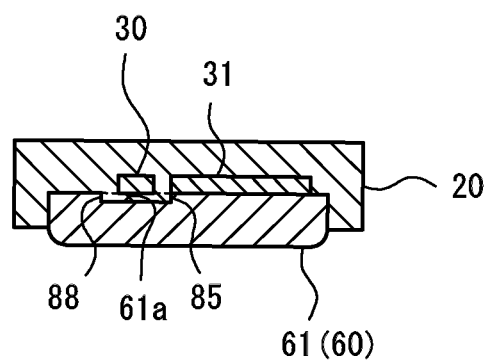
FIG. 6B is a cross-sectional view taken along line VIB-VIB in FIG. 5.

More specifically, as illustrated in FIG. 6B, the electrode 61 of the body sensor 60 has a flat upper surface and a recess 61a formed in the upper surface. The extension layer portion 85 is formed so as to fill the recess 61a, and a stretchable wiring line 30 is formed on the extension layer portion 85. Accordingly, the stretchable wiring line 30 is electrically isolated from the electrode 61 by the extension layer portion 85. The extension layer portion 85 formed in the flexible substrate 20 separates the stretchable wiring line 30 from the electrode 61 in the thickness direction. The extension layer portion 85 serves as an isolation portion 88 in which the stretchable wiring line 30 and the electrode 61 do not have a contact portion. By providing the isolation portion 88, the stretchable wiring lines 30 can be disposed without detouring around in the stretchable wiring member 13. The isolation portion 88 also reduces the likelihood of breakage of the stretchable wiring lines 30. Another difference is that the stretchable wiring member 11 has an electroconductive rubber connector 50 disposed only at one end, whereas the stretchable wiring member 13 has electroconductive rubber connectors 50 disposed at respective ends thereof. Moreover, the stretchable wiring member 13 has a conduction-path-shape retaining member 90 disposed under the electroconductive rubber connector 50, whereas the stretchable wiring member 11 does not have this member.

The conduction-path-shape retaining member 90 is disposed so as to overlap the electrode 51 as viewed in the thickness direction of the stretchable wiring member 13. The conduction-path-shape retaining member 90 can reduce the deformation of the electrode 51 that is vulnerable to deformation in the stretching direction when the stretchable wiring member 13 is stretched. The conduction-path-shape retaining member 90 is formed like a plate. The conduction-path-shape retaining member 90 may be made of a material having such hardness that the conduction-path-shape retaining member 90 is not stretched in in-plane directions of the plate. More specifically, the conduction-path-shape retaining member 90 may be formed, for example, of a resin film, such as a polyethylene terephthalate film or a polyimide film, a hard resin compact, such as a hard resin substrate, or a ceramic substrate or a metal film. It is sufficient that the conduction-path-shape retaining member 90 has a hardness to the level of the flexible substrate 20 or more. Accordingly, a thermosetting rubber and a thermoplastic elastomer that are harder than the flexible substrate 20 can be used.

The stretchable wiring member 13 can be manufactured by producing the first segment and the second segment of the flexible substrate 20 each having a half thickness and by laminating the first segment and the second segment on each other, which is similar to the manufacturing method described in the first embodiment. The first segment of the stretchable wiring member 13 having the body sensors 60 is formed first. The flexible substrate 20 is molded integrally with the body sensors 60 in such a manner that the upper surface of each body sensor 60 is flush with the surface of the extension layer portion 80. Subsequently, the stretchable wiring lines 30 are formed thereon by printing. The first segment is laminated on the second segment of the flexible substrate 20 of the stretchable wiring member 13. The stretchable wiring member 13 can be thus manufactured.

In the stretchable wiring member 13, the stretchable wiring line 30 connected to the second electrode 61 is laminated on the first electrode 61 in the thickness direction of the stretchable wiring member 13 with the extension layer portion 80 interposed therebetween. In other words, the stretchable wiring line 30 connected to the second electrode 61 can be spaced from the first electrode 61 by the insulating extension layer portion 85. Accordingly, the stretchable wiring line 30 can be laminated on the first electrode 61 with no electrical connection therebetween, which can reduce the width of the stretchable wiring member 13.

Figure 7:
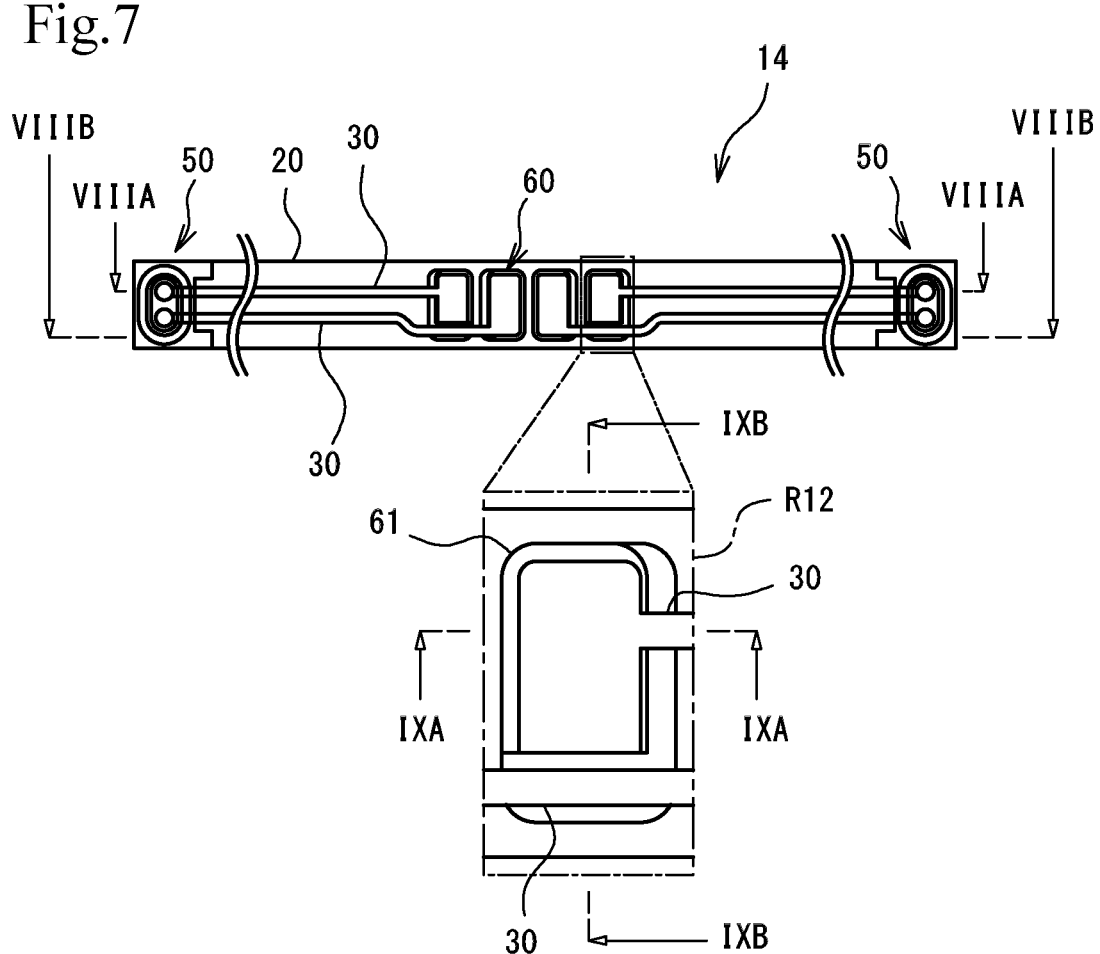
FIG. 7 is a schematic plan view illustrating a stretchable wiring member according to a third embodiment, in which a flexible substrate is assumed to be transparent.
Figure 8A:
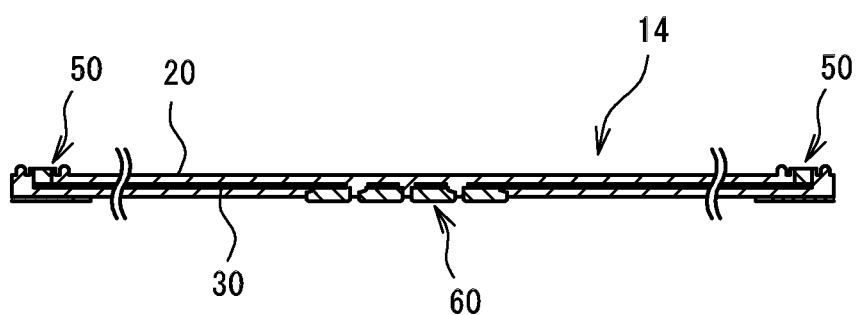
FIG. 8A is a cross section taken along line VIIIA-VIIIA in FIG. 7
Figure 8B:
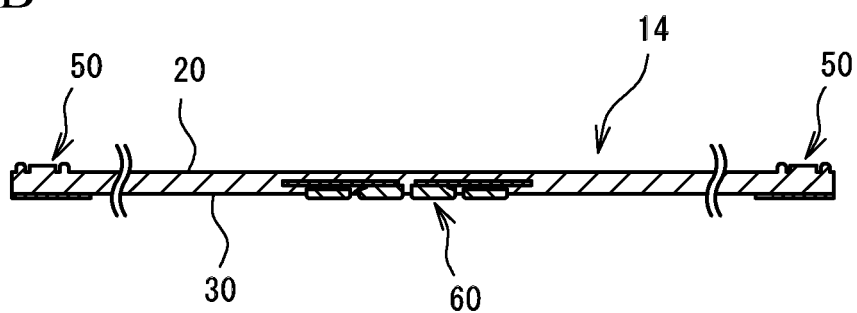
FIG. 8B is a cross section taken along line VIIIB-VIIIB in FIG. 7.

Third Embodiment [FIGS. 7 to 9]

Figure 9A:
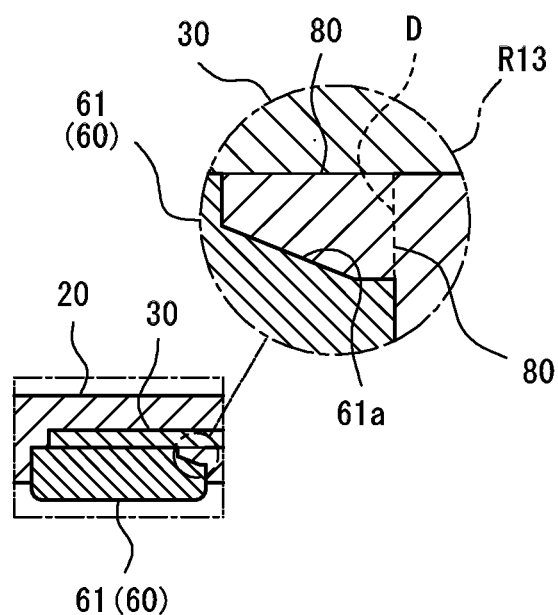
FIG. 9A is a cross section taken along line IXA-IXA in FIG. 7
Figure 9B:
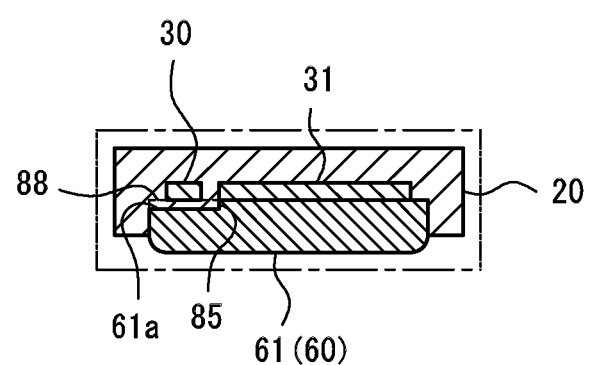
FIG. 9B is a cross section taken along line IXB-IXB in FIG. 7.

A stretchable wiring member 14 according to a third embodiment is configured to have both features of the first embodiment and the second embodiment. In other words, of the four body sensors 60 illustrated in FIG. 7, each of two peripherally disposed body sensors 60 illustrated in a partially enlarged region R12 of FIG. 7 has two types of extension layer portions, in other words, the extension layer portion 80 and the extension layer portion 85 (FIG. 9). More specifically, as illustrated in a partially enlarged region R13 of FIG. 9A, the extension layer portion 80 included in the stretchable wiring member 14 is similar to the extension layer portion 80 of the stretchable wiring member 11 of the first embodiment. In addition, as illustrated in FIG. 9B, the stretchable wiring member 14 also has an isolation portion 88 that includes an extension layer portion 85, which is similar to the extension layer portion 85 of the stretchable wiring member 13 of the second embodiment.

As illustrated in FIG. 7, the stretchable wiring member 14 includes four body sensors 60 that have respective extension layer portions 80. Accordingly, each stretchable wiring line 30 extending from the corresponding body sensor 60 can be prevented from breaking at the boundary between the stretchable wiring line 30 and the body sensor 60. In addition, the two peripherally disposed body sensors 60 in FIG. 7 have respective extension layer portions 85. Accordingly, the stretchable wiring line 30 that overlaps each of the peripherally disposed body sensors 60 can be prevented from breaking at the boundary at which the stretchable wiring line 30 is drawn out from the overlapping portion.

Fourth Embodiment [FIG. 10]

A stretchable wiring member 15 according to a fourth embodiment has an extension layer portion 80 disposed at the second connector 70 disposed at an end of the stretchable wiring member 15. In the first embodiment, the second connector 70 of the stretchable wiring member 11 has the holding member 71 for fixing the terminal portion P2 of the flexible cable P1 to the flexible substrate 20, and the holding member 71 is formed of a member different from the flexible substrate 20. In the stretchable wiring member 15, however, a portion of the flexible substrate 20 serves as the holding member 71.

As illustrated in FIG. 10, the stretchable wiring member 15 has a recess 61a formed by chipping off an edge portion of the flexible cable P1. The flexible substrate 20 enters the recess 61a and thereby forms the extension layer portion 80. In the stretchable wiring member 15, due to the extension layer portion 80 being provided, the stretchable wiring line 30 extending from the connection portion of the flexible cable P1 can be prevented from breaking in the vicinity of the connection portion between the stretchable wiring line 30 and the flexible cable P1.

Modification Example 4-1 [FIG. 11]

In the stretchable wiring member 16 of the present embodiment, a connection object P formed of a hard member, such as the flexible cable P1, is embedded in the flexible substrate 20 at the second connector 70, as illustrated in FIG. 11. The stretchable wiring member 16 also has the extension layer portion 80, which is similar to the stretchable wiring member 15 of the fourth embodiment. In the stretchable wiring member 16 having the above configuration, the stretchable wiring line 30 can be prevented from breaking easily at the boundary between the stretchable wiring line 30 and the flexible cable P1.

Figure 12A:
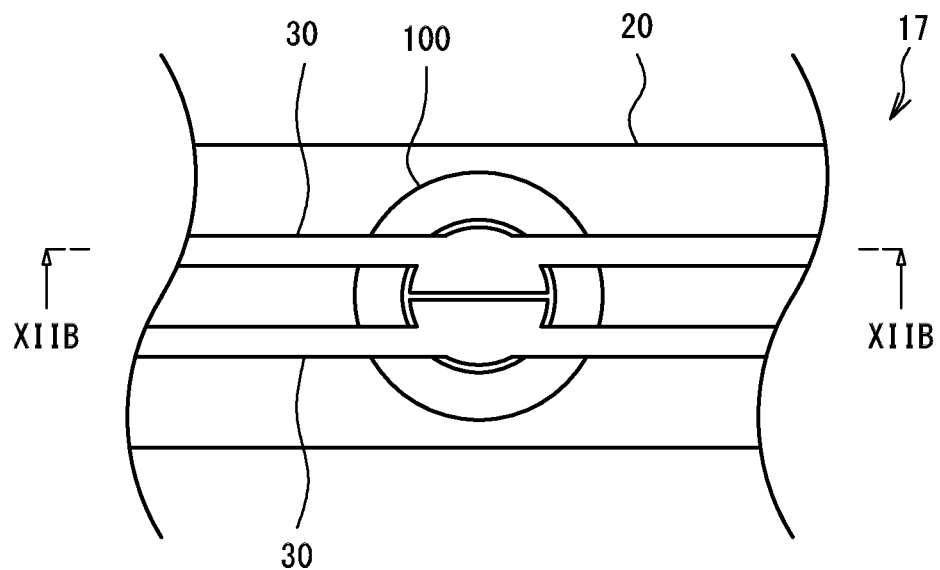
FIG. 12A is a bottom view of an essential part of the stretchable wiring member and FIG. 12B is a cross section taken along line XIIB-XIIB in FIG. 12A.
Figure 12B:
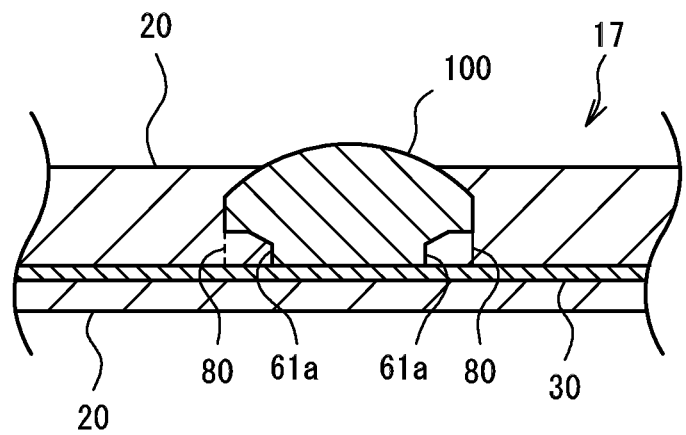

Fifth Embodiment [FIGS. 12]

The stretchable wiring member 17 of the present embodiment includes an insulating hard member 100 that is different from the above-described contact point member 40. The extension layer portion 80 is formed in such a manner that when the hard member 100 is projected on a picture plane in the thickness direction of the stretchable wiring member 17, a contact surface between the flexible substrate 20 and the stretchable wiring line 30 is present inside the projected hard member 100.

The hard member 100 is made of an insulating hard material and has such a rigidity as not to be stretched in the stretching direction of the flexible substrate 20. As illustrated in FIG. 12, an example of the hard member 100 has a circular shape as viewed in plan. The shape of the hard member 100, however, is not limited to the circular shape. For example, the insulating hard material is a bendable resin film or a hard resin substrate, a thin tabular member, such as a ceramic substrate, or a lump-like member, such as a button-like member as illustrated in FIG. 12. The hard member 100 is preferably made of polyimide, phenolic resin, or epoxy resin. Although a lump-like (button-like) hard member 100 is illustrated in FIG. 12, the hard member 100 may be shaped like a film (or a flake) made of a dielectric material and may be configured to serve as a touch sensor.

The embodiments described above are examples according to the present invention. The embodiments may be modified or known techniques may be added thereto or combined therewith without departing from the scope of the invention. Such modifications, additions, and combinations are to be within the scope of the present invention.

Figure 13A:
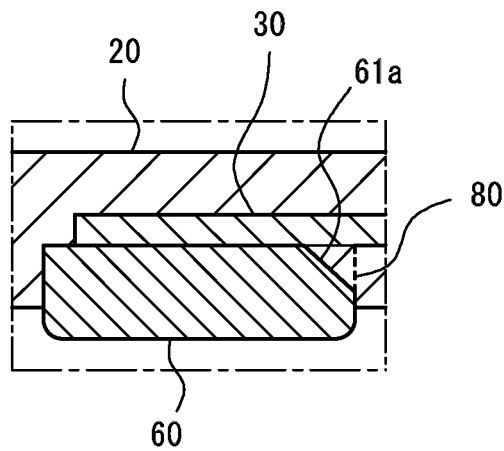
FIG. 13 are cross-sectional views for explanation of modification examples of an extension layer portion, in which any of FIGS. 13A to 13C corresponds to the partially enlarged region R5 of FIG. 2.
Figure 13B:
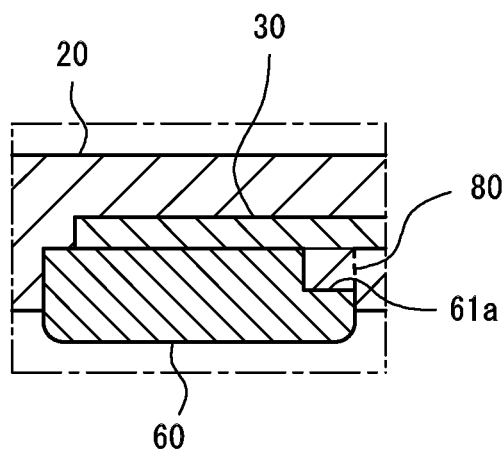
Figure 13C:
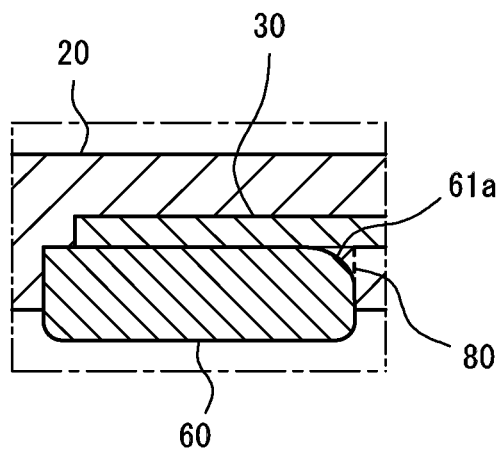

For example, the extension layer portion 80 is not limited to that of the stretchable wiring member 11 of the first embodiment illustrated in FIG. 2. The extension layer portion 80 may assume various other shapes depending on the shape of the recess 61a of the electrode 61. For example, as illustrated in FIG. 13A, the recess 61a of the electrode 61 may be formed as a declining surface that declines from an end of the contact surface with the stretchable wiring line 30 so as to be gradually separated from the stretchable wiring line 30. In this case, the extension layer portion 80 is shaped so as to fill the gap between the declining surface and the stretchable wiring line 30. Alternatively, as illustrated in FIG. 13B, the recess 61a of the electrode 61 may be formed like a rectangular step. In this case, the extension layer portion 80 is shaped like a cuboid so as to fill the gap between the rectangular step and the stretchable wiring line 30. Still alternatively, as illustrated in FIG. 13C, the recess 61a of the electrode 61 may be formed like a curved surface. In this case, the extension layer portion 80 is shaped so as to fill the gap between the curved surface and the stretchable wiring line 30.

Reference Signs List 11 to 17 stretchable wiring member
20 flexible substrate
20a front surface
20b back surface
20c waterproofing rib
30 stretchable wiring line
31 contact portion
40 contact point member
50 electroconductive rubber connector
51 electrode
51a first contact end
51b second contact end
52 cover portion
60 body sensor
61 electrode (hard member)
61a recess
70 second connector
71 holding member
80, 85 extension layer portion
88 isolation portion
100 conduction-path-shape retaining member
100 hard member
D boundary surface P connection object
P1 flexible cable
P2 terminal portion
P3 wiring
R1 to R13 partially enlarged region

The invention claimed is:

1. A stretchable wiring member comprising:
   a flexible substrate having stretchability;
   a stretchable wiring line disposed along the flexible substrate and configured to be stretched in association with stretching deformation of the flexible substrate; and
   hard members that are located under the stretchable wiring line and harder than the flexible substrate, wherein
   the flexible substrate has an extension layer portion interposed between the hard member and the stretchable wiring line,
   the stretchable wiring line has a contact portion that is made of a same material as the stretchable wiring line, and the contact portion has that an end portion of the stretchable wiring line which is expanded in a width direction of the stretchable wiring line and, narrower than a width of the hard members,
   the contact portion is formed at an end portion of the stretchable wiring line on a side overlapping with the hard members, and
   the stretchable wiring line extends from an outer periphery of one of the hard members to a first contact point member located at one end of the stretchable wiring member, and from an outer periphery of another of the hard members to a second contact point member located at an another end of the stretchable wiring member,
   the contact point members being connector portions of the stretchable wiring member that electrically connect the stretchable wiring lines to connection objects.

2. The stretchable wiring member according to claim 1, wherein
   the hard member has a recess formed at a position between the hard member and the stretchable wiring line, and the extension layer portion is disposed in the recess.

3. The stretchable wiring member according to claim 1, wherein the hard member is an electroconductive member.

4. The stretchable wiring member according to claim 1, wherein the hard member is an electrode.

5. The stretchable wiring member according to claim 1, wherein the hard member is electrically connected to the stretchable wiring line.

6. The stretchable wiring member according to claim 1, wherein the hard member is an electroconductive rubber that is made of at least one of a thermosetting rubber and a thermoplastic elastomer and in which an electroconductive filler is dispersed.

7. The stretchable wiring member according to claim 1, wherein
   the stretchable wiring line is spaced from the hard member in a thickness direction of the flexible substrate, and
   the stretchable wiring member further comprises an isolation portion that isolates the stretchable wiring line from the hard member.

8. The stretchable wiring member according to claim 1, wherein the hard member is an insulating member.

9. The stretchable wiring member according to claim 1, wherein the extension layer portion has a portion near the center of the hard member and an outer portion as viewed in plan, and the outer portion is formed to be thicker than the portion near the center of the hard member.

10. The stretchable wiring member according to claim 1, wherein the flexible substrate and the stretchable wiring line contain a silicone rubber component.

11. The stretchable wiring member according to claim 1, wherein when the hard member is viewed in plan, a boundary of the contact area between the stretchable wiring line and the hard member is positioned inside an outer periphery of the hard member.

12. The stretchable wiring member according to claim 1, wherein
    the extension layer portion is located inside an outer edge of the hard member and outside an outer edge of the contact portion in a plan view.

13. The stretchable wiring member according to claim 1, wherein an adhesive strength between the stretchable wiring line and the flexible substrate is set to be greater than a tensile strength at break of the stretchable wiring line.

* * * * *